United States Patent [19]

Kaufman

[11] Patent Number: 5,002,874

[45] Date of Patent: Mar. 26, 1991

[54] GENETICALLY ENGINEERED EUCARYOTIC HOST CELLS CAPABLE OF EXPRESSING MODIFIED FORMS OF EIF-2α

[75] Inventor: Randal J. Kaufman, Boston, Mass.

[73] Assignee: Genetics Institute, Inc., Cambridge, Mass.

[21] Appl. No.: 561,217

[22] Filed: Jul. 30, 1990

Related U.S. Application Data

[63] Continuation of Ser. No. 98,000, Sep. 17, 1987, abandoned.

[51] Int. Cl.$^5$ .................... C12N 7/00; C12N 15/00
[52] U.S. Cl. ........................ 435/69.1; 435/172.3; 435/240.1; 435/240.2; 435/235; 435/320.1; 536/27; 935/34; 935/37; 935/66; 935/68; 935/69; 935/70; 935/71
[58] Field of Search ............... 435/240.1, 240.2, 69.1, 435/172.3, 320, 235, 948; 935/34, 37, 66, 68, 69, 70-71; 536/27

[56] References Cited

PUBLICATIONS

Wittenhall, R. E. H. et al., 1986 (Sep. 25), J. Biol. Chem. 261(27), 12444–12447.

Morinager, Y. et al., 1984, Bio/Technology 2, 636–639.

Colhurst, P. R. et al., Jul. 1987, Eur. J. Biochem. 166:357–363.

Kudlicki, W. et al., 1987, FEBS Letter 215(1), 16–20 (May 1987).

Pathak, U. K. et al., Feb. 1988, Mol. Cell Biol 8(2), 993–995.

Ernst, H. et al., Jan. 25, 1987, J. Biol. Chem. 262(3), 1206–1212.

*Primary Examiner*—Robin L. Teskin
*Attorney, Agent, or Firm*—Bruce M. Eisen

[57] ABSTRACT

Eucaryotic host cells are disclosed which contain a DNA molecule encoding an eIF-2α mutant and preferably a DNA sequence encoding a desired heterologous protein. The DNA sequences are linked to expression control sequences permitting expression of the mutant eIF-2α gene and the heterologous gene. Culturing such cells provides a method for the production of the desired heterologous protein. The mutations eliminate one or both serine residues at positions 48 and 51 of the eIF-2 sequence. In another aspect of the invention, the eIF-2 5'-untranslated sequence was observed to have effects on translation of heterologous mRNAs.

10 Claims, No Drawings

GENETICALLY ENGINEERED EUCARYOTIC HOST CELLS CAPABLE OF EXPRESSING MODIFIED FORMS OF EIF-2α

This application is a continuation of application Ser. No. 07/098,000, filed Sep. 17, 1987, now abandoned.

BACKGROUND

It has been previously demonstrated that a critical control in the translation of mRNAs is at the level of phosphorylation of the eukaryotic initiation factor 2-alpha (eIF-2α). Two protein kinases have been shown to regulate initiation of translation by phosphorylation of this factor. The hemin-controlled repressor of protein synthesis (HCR) has been studied in reticulocytes and is activated by various stimuli including hemin deprivation and heat treatment. The double-stranded RNA activated inhibitor (DAI) is induced by interferon and its activity is dependent on double stranded RNA. It has previously been thought that phosphorylation by these kinases results in a general suppression of translation of cellular mRNAs. Several viruses encode specific regulatory mechanisms which can circumvent the translation inhibition imposed by activation of these kinases. One well studied example is adenovirus where a specific RNA gene product, the adenovirus associated RNA (VA RNA), can block the DAI kinase. Upon viral infection, the host cell induces and activates the DAI kinase as part of its antiviral response. Adenovirus can circumvent this antiviral response by the expression of the VA gene which directly blocks the kinase activity. Adenovirus mutants in the VA gene produce functional mRNAs but they are not translated as a result of the DAI kinase activation. In previous work we observed in a similar manner that transfected COS monkey cells exhibit suppressed translation and that the inefficient translation is restricted to mRNAs derived from the plasmid DNA. No translation suppression was observed on host mRNAs. Thus, there appeared to be a specificity in the translational block. The reason for this specificity is not known.

The research resulting in the present invention involved studying the effect of expression of eIF-2α at high levels and by expression of modified forms of eIF-2α which may not be susceptible to phosphorylation. The results of these studies provide (1) insight into the potential importance of translational control and (2) eucaryotic expression systems permitting the expression of foreign proteins at high level in animal cells.

DESCRIPTION OF THE INVENTION

This invention provides improved eucaryotic host cells for the expression of heterologous genes. The eucaryotic host cells of this invention are preferably mammalian cells, such as COS, CV-1, NIH 3T3, CHO, HeLa, etc. cells which contain a DNA molecule encoding the peptide sequence of a mutant form of eIF-2α operatively linked to an expression control sequence, permitting expression of the mutant eIF-2α gene. Certain of the mutant eIF-2α proteins useful in this invention are characterized by their partial or complete lack of susceptibility to phosphorylation. Others are characterized by their ability to enhance translation of mRNAs in transfected cells.

These mutant eIF-2α proteins are characterized structurally by the sequences shown in Table 1, except for modification at one or both of Ser-48 and Ser-51. Such modifications within the ambit of this invention include deletion of one or both serines; replacement of one or both serines with different amino acids; replacement of one or both serines with a di-, tri- or oligopeptide sequence which preferably does not contain serine; or combinations of the above. Most preferably, one or both serines are simply replaced with different amino acids. Methods for the construction of DNA sequences encoding illustrative mutant eIF-2α genes of this invention are provided below, as are methods for design and construction of vectors for incorporating such genes into the genome of eucaryotic cells.

TABLE 1

DNA (single strand) and peptide sequence of eIF-2α: rat and human

```
                  10           20           30
human  - - G- - - - - A-  - - - - - - C- T-  - C- - - - - - - -   - - -   - - - - - -
rat    GTT CGG GAT T  CAC ACA TAC A  CTT CAG AAT G  CCG GGT CTA
rat                                                 Met Pro Gly Leu 60
       - - -  - - -  - - -  - - -  - - -  - - -   - - -  - - -  - - -  - - -  - - -  - - G - - -
       AGT    TGT    AGA    TTT    TAT    CAA    CAC    AAA    TTT    CCT    GAG    GTC    GAA
       Ser    Cys    Arg    Phe    Tyr    Gln    His    Lys    Phe    Pro    Glu    Val    Glu 90                                              120
       - - -  - - -  - - -  - - -  - - -  - - -  - - C - - -  - - -  - - -  - - -  - - -  - - -  - - -
       GAT    GTA    GTG    ATG    GTG    AAT    GTA    AGA    TCC    ATT    GCT    GAA    ATG    GGG
       Asp    Val    Val    Met    Val    Asn    Val    Arg    Ser    Ile    Ala    Glu    Met    Gly 150
human  - - T - - -  - - -  - - -  - - -  - - -  C- -  - - -  - - C - - C - - -  - - -  - - -  - - -
rat    GCC    TAT    GTC    AGC    TTG    TTG    GAA    TAT    AAT    AAC    ATT    GAA    GGC
rat    Ala    Tyr    Val    Ser    Leu    Leu    Glu    Tyr    Asn    Asn    Ile    Glu    Gly 180
       - - -  - - -  - - -  - - -  - - -  - - -  - - -  - - - - - -  A- G - - -  - - -  - - -
       ATG    ATT    CTT    CTT    AGT    GAA    TTA    TCC    AGA    CGA    CGT    ATC    CGT
       Met    Ile    Leu    Leu    Ser    Glu    Leu    Ser    Arg    Arg    Arg    Ile    Arg 210                                              240
       - - -  - - C - - -  - - -  - - C - - -  - - -  - - -  - - -  - - G - - - -  - - G - - -  - - G
       TCT    ATA    AAC    AAA    CTG    ATC    CGA    ATT    GGC    AGA    AAT    GAA    TGT    GTA
       Ser    Ile    Asn    Lys    Leu    Ile    Arg    Ile    Gly    Arg    Asn    Glu    Cys    Val
```

TABLE 1-continued
DNA (single strand) and peptide sequence of eIF-2α: rat and human

```
                                    270
human    - - -  - - -  - - -  - -G  - - -  - -C  - - -  - - -  - - -  - - -  - -T  - - -
rat      GTT    GTC    ATT    AGA   GTG    GAT   AAA    GAA    AAA    GGA    TAT    ATA    GAT
rat      Val    Val    Ile    Arg   Val    Asp   Lys    Glu    Lys    Gly    Tyr    Ile    Asp 300
         - - -  - - -  - - -  - - -  - - -  - - -  - - -  - - -  - - -  - - -  - - -
         TTG    TCA    AAA    AGA    AGA    GTT    TCT    CCA    GAG    GAA    GCA    ATC    AAA
         Leu    Ser    Lys    Arg    Arg    Val    Ser    Pro    Glu    Glu    Ala    Ile    Lys 330                                                                                360
         - - -  - - -  - - -  - - -  - - -  - - -  - - -  - - -  - - -  - - -  - - -  - - -  - - -
                TGT    GAA    GAC    AAA    TTC    ACA    AAA    TCC    AAA    ACT    GTT    TAT    AGC    ATT
                Cys    Glu    Asp    Lys    Phe    Thr    Lys    Ser    Lys    Thr    Val    Tyr    Ser    Ile 390
human    - - -  - -T  - - -  - - -  - - -  - - -  - - -  - -G  - - -  - -A  - -C  - - -  - - -  - - -
rat      CTT    CGC    CAT    GTT    GCT    GAG    GTA    TTA    GAG    TAT    ACC    AAG    GAT
rat      Leu    Arg    His    Val    Ala    Glu    Val    Leu    Glu    Tyr    Thr    Lys    Asp 420
         - - -  - - -  - - -  - - -  - - -  - - -  - - -  - - -  - - -  - - -  - - -  - - -
         GAG    CAG    CTG    GAA    AGC    CTA    TTC    CAG    AGG    ACT    GCC    TGG    GTC
         Glu    Gln    Leu    Glu    Ser    Leu    Phe    Gln    Arg    Thr    Ala    Trp    Val 450                                                                   480
         - - -  - - -  - - -  - - -  - - -  - - -  - - -  - - -  - - -  - - -  - - -  - - -  - - -
         TTT    GAT    GAC    AAG    TAC    AAG    AGA    CCT    GGA    TAT    GGT    GCC    TAT    GAT
         Phe    Asp    Asp    Lys    Tyr    Lys    Arg    Pro    Gly    Tyr    Gly    Ala    Tyr    Asp 510
human    - -A  - - -  - - -  - - -  - - -  - - -  - - -  - - -  - - -  - -T  - - -  - - -
rat      GCC    TTT    AAG    CAT    GCA    GTC    TCA    GAC    CCA    TCT    ATC    TTG    GAT
rat      Ala    Phe    Lys    His    Ala    Val    Ser    Asp    Pro    Ser    Ile    Leu    Asp 540
         - - -  - - -  - - -  - - -  - - -  - - -  - - -  - - -  C-  G - -  - - -  - - -  - - -  - - -
         AGT    TTA    GAT    TTG    AAT    GAA    GAT    GAA    AGA    GAA    GTA    CTC    ATT
         Ser    Leu    Asp    Leu    Asn    Glu    Asp    Glu    Arg    Glu    Val    Leu    Ile 570                                                                   600
         - -T  - - -  - -T  - - -  - - -  - -C  - - -  - - -  - - -  - -G  - - -  - - -  - -A  - - -
         AAC    AAT    ATC    AAT    AGG    CGT    TTG    ACC    CCA    CAA    GCT    GTC    AAG    ATT
         Asn    Asn    Ile    Asn    Arg    Arg    Leu    Thr    Pro    Gln    Ala    Val    Lys    Ile 630
human    - - -  - - -  - - -  - - -  - -A  - -G  - - -  - -T  - - -  - - -  - -T  - - -  - - -
rat      CGA    GCA    GAT    ATT    GAG    GTA    GCT    TGC    TAT    GGT    TAC    GAA    GGC
rat      Arg    Ala    Asp    Ile    Glu    Val    Ala    Cys    Tyr    Gly    Tyr    Glu    Gly 660
         - - -  - - -  - - -  - - -  - - -  - - -  - - -  - -A  - - -  - - -  - - -  - - -
         ATT    GAT    GCT    GTA    AAA    GAA    GCC    CTG    AGA    GCA    GGT    TTG    AAT
         Ile    Asp    Ala    Val    Lys    Glu    Ala    Leu    Arg    Ala    Gly    Leu    Asn 690 Asn                                                               720
         - - -  - - -  - - -  - - -  - -A-  - - -  - - -  - -T  - - -  - - -  - - -  - - -  - - -
         TGT    TCT    ACA    GAA    ACC    ATG    CCC    ATC    AAG    ATT    AAT    CTA    ATA    GCT
         Cys    Ser    Thr    Glu    Thr    Met    Pro    Ile    Lys    Ile    Asn    Leu    Ile    Ala 750
human    - -T  - -T  C- -  - - -  - -A  - - -  - -T  - -G  - -A  - - -  - -G  - - -  - -A
rat      CCA    CCC    AGG    TAT    GTG    ATG    ACA    ACA    ACG    ACC    CTA    GAG    AGG
rat      Pro    Pro    Arg    Tyr    Val    Met    Thr    Thr    Thr    Thr    Leu    Glu    Arg 780 Ser
         - - -  - - -  - -C  - -T  - - -  - -C  - - -  - G-  - -A  - - -  - - -  - -T  - -T
         ACA    GAA    GGA    CTC    TCT    GTT    CTC    AAT    CAG    GCT    ATG    GCA    GTC
         Thr    Glu    Gly    Leu    Ser    Val    Leu    Asn    Gln    Ala    Met    Ala    Val 810                                                                   840
         - - -  - - -  - -G  - - -  - - -  - - -  - - -  - -A  - - -  - - -  - -T  - - -  - - -  - - -
         ATC    AAA    GAA    AAG    ATT    GAG    GAG    AAG    AGG    GGA    GTG    TTC    AAT    GTT
         Ile    Lys    Glu    Lys    Ile    Glu    Glu    Lys    Arg    Gly    Val    Phe    Asn    Val
```

-continued

```
                                    870
human - - A - - -  - - -  - - -  - - -  - - -  - -C - - -  - - -  - - -  - - -  - - -
rat    CAG ATG GAG CCC AAA GTG GTT ACA GAT ACA GAT GAG ACT
rat    Gln Met Glu Pro Lys Val Val Thr Asp Thr Asp Glu Thr Met  900
        - - -  - - -  - -G - - -  - - -  A- -  - -G  A- -  - - -  - -A - - -  - - -  - - -
        GAA CTT GCA AGG CAG CTG GAA CGG CTT GAG AGA GAA AAT
        Gly Leu Ala Arg Gln Leu Glu Arg Leu Glu Arg Glu Asn 930                                         960
        - -C - - -  - - -  - - -  - - -  - - -  - - -  - - -  - - -  - - -  - - -  - - -  - - -
        GCA GAA GTG GAT GGA GAT GAT GAT GCA GAA GAA ATG GAA GCC
        Ala Glu Val Asp Gly Asp Asp Asp Ala Glu Glu Met Glu Ala 980          990         1000         1010         1020
                                AG
human - - -  - - -  - - -  - - -  - - -  - T- -G - - -G- - - - - -  T - - - - - - - - - -  - - -AC- -AG-  - - - - -G- - -C
rat    AAA GCT GAA GAT TAA CCTTT TGGAAAACAG TCCAATTTAA GGAGTACGAA GCAGCCCTTT
rat    Lys Ala Glu Asp End 1030         1040         1050         1060         1070         1080         1090
                                                                                      T
        - - - - - - - - - -  -T- - - - - - - -  - - - - - - - - - -  - - - - - - - - - -  - - - - - - - - - -  - - - - - - - - - -  - - - - - - - - -T-
        CTGGCTGTAA ACCCTAGACT TGAAAGTTTT CCAGTATTGA AAACTTCAAA GCTGAATATT TTTATTTCCA 1100         1110         1120         1130         1140         1150         1160
                 T                   G
human - - - - - - - - -  A -G- - -A- - -  G AT- - - - -  CA-  - - - - - - - - - -  - - AA- - - - -  - - - - - - G- - -  - -C- - -A- - -
rat    AGTATTTAAG TATTCGACAA GCCAGAATCT AAATGCCCTC CTTCATGTCA GCTGTTTTCA CATAGTGGCT 1170         1180         1190         1200         1210         1220         1230

-C- - - - -T-T G- - -A- - - - -  - - - - - - - - - -  -C-C- - - -C-  -T- - - - - - - -  - -C- -T- -GA AT- - -T- - - -
        CTAACACCTC AAGCGTTTTT AAGGGAGTGG CTTGATTTGA CCAGAGACAA ATGTTAAACC GCAGTCCTAA 1240         1250         1260         1270         1280         1290         1300
                                                      CT          ATGCCTCAC
human - - - - - - - - - -  -T- A- - -C- -  - - - - - - - - - -  - - -CA- - - - -  - - - - - - - - -T-C-  A- - -C- - - -  T- -G- - - - - -
rat    AATTGGGCTT GCGGTTTTCA TTTCTGATGT CTCTGGATTG GCACCCTTAT GGTTTAGAGA ATTACCAGGG 1310         1320         1330         1340         1350         1360         1370

- -AT- CA- GG - A- - - - - - - - -  - - -T- - - - - - - - - - - - -  - - -T- - - - - - - - - - - -  - - - - - - - - - - - - - - -
        GCTCCAGACA CCAACAATCC CAACCTTTCT ATATAAAATG TACTCAAGCA AACATCAAAT AAATTTCTGGGATATT
```

"-'s" in the human sequence indicate conserved sequences; extra nucleotides in the human sequence are shown above the human sequence.

Typically, conventional methods and conventional transformation or expression vectors may be used to transfect or transform eucarotic cells with a mutant eIF-2α gene of this invention functionally linked to a suitable expression control sequence.

In one embodiment of the invention, the eucaryotic cell contains multiple copies of the mutant eIF-2α gene. Such cells may be prepared by transfecting the starting cells with a vector containing (1) the desired mutant eIF-2α gene operatively linked to a suitable expression control sequence, and (2) a selectable, amplifiable marker operatively linked to the same or a different expression control sequence. Elements (1) and (2) may be inserted into the eucaryotic cells on unlinked or linked vectors, as is known in the art. Transformants may then be grown under selective pressure using a selection agent appropriate for the marker, as is well known in the art, to amplify copy number of the transfected or transformed genes.

Of particular use are eucaryotic host cells containing a mutant eIF-2α gene as described above, which further contain a heterologous DNA sequence encoding a desired heterologous protein operatively linked to an expression control sequence permitting expression of the heterologous DNA sequence. Preferably the eucaryotic cell is transfected or transformed with a vector containing the heterologous DNA sequence and expression control sequence, as described above, in association with a linked or unlinked vector containing a selectable, amplifiable marker permitting amplification of gene copy number of the heterologous DNA sequence, as is known in the art. The heterologous DNA sequence and/or the mutant eIF-2α gene may alternatively be inserted into the eucaryotic cells on multiply-amplifiable vectors containing more than one selectable, amplifiable marker as described in PCT/US86/02326, incorporated herein by reference.

Heterologous proteins include among others thrombolytic agents such as human tissue-type plasminogen activator (t-PA) and urokinase (u-PA); coagulation-related proteins such as human Factor VIII:c, Factor IX and Von Willebrand factor; anti-thrombin III; erythropoietin; superoxide dismutase; thrombomodulin; lymphokines such as interleukins, interferons, tumor necrosis factor and colony stimulating factors including GM-CSF, G-CSF, M-CSF, multi-CSF, meg-CSF, CSF-1, etc.; growth hormones such as human, bovine, etc. growth hormones; other hormones; enzymes; and variants of such proteins.

Eucaryotic host cells which express both the mutant eIF-2α gene and the heterologous DNA sequence may be cultured by conventional techniques as a method for the production of the heterologous protein. The heterologous protein so produced may then be identified, recovered and purified by conventional means.

Another aspect of this invention provides for improved expression vectors for use in expressing heterologous proteins in eucaryotic cells. The improved vectors are characterized by containing an eIF-2α 5' untranslated DNA sequence or a truncated sequence derived therefrom linked to, and upstream (i.e., 5'-) of, the DNA sequence encoding the heterologous protein. The DNA sequence encoding the heterologous protein is of course operatively linked to an expression control sequence, and the vector may also contain other conventional elements typically found in expression vectors, including e.g., one or more selectable, amplifiable markers; enhancers; bacterial origin of replication; antibiotic resistance gene, etc.. An exemplary eIF-2α 5' untranslated sequence is provided in the Examples below. The sequence or truncated derivatives thereof may be conveniently synthesized and inserted into the vector by conventional means. The eIF-2α 5' untranslated region may be inserted directly upstream of the coding region for the heterologous protein, i.e. replacing the native 5' untranslated region. Alternatively, part or all of the native 5' untranslated region may be left intact, downstream of the inserted eIF-2α 5' untranslated region.

The improved vectors of this aspect of the invention take advantage of the unexpected and surprising observation made in the course of the research disclosed herein of (1) the ability of eIF-2α mRNA to be translated efficiently in the presence of eIF-2α phosphoylation, and (2) that this property of eIF-2α mRNA is dependent on nucleotide sequences within the 5' untranslated region thereof. When these sequences are introduced into an expression vector so that they are present in the 5' untranslated region of a desired protein-coding sequence, then the mRNA encoding the desired protein and containing the eIF-2α 5' untranslated sequences may be efficiently translated under conditions in which eIF-2α is phosphorylated, e.g. heat shock, serum deprivation, etc.

Eucaryotic cells may be transfected or transformed with vectors of this aspect of the invention by conventional methods, and the resulting cells may be used in a method for the production of the heterologous protein. The method comprises culturing the resulting cells under suitable conditions, as is known in the art, permitting production of the heterologous protein, which may then be identified, recovered and purified by conventional means.

A. eIF-2α and mutants thereof

A cDNA gene encoding human eIF-2α has a sequence substantially as indicated in Table 1. The cDNA may be obtained by Eco RI and Sac I digestion of plasmid pMT2VA⁻eIF2 (ATCC No. 67511), identified with standard hybridization techniques using oligonucleotides derived from the sequence of Table 1, and gel-purified, also by conventional methods. DNA sequences encoding eIF-2α mutants of this invention may be prepared by conventional oligonucleatide-directed mutagenesis of the DNA sequence of Table 1. Such methods of mutagenesis include the M13 system of Zoller and Smith, 1982, Nucleic Acids Res. 10:6487–6500; 1983, Methods Enzymol. 100:468–500; and 1984, DNA 3:479–488, using single stranded DNA, and the method described by Morinaga et al., 1984, Bio/Technology 2:636–639, using hetroduplexed DNA. eIF-2α cDNAs from other species (i.e., non-human) may be cloned using the human cDNA sequence or oligonucleotides derived therefrom for identification of the desired sequence. Corresponding non-human eIF-2α DNA sequences may be used as equivalent alternatives to the human DNA sequence in the various embodiments of this invention.

B. Expression

The eukaryotic cell expression vectors described herein may be synthesized by techniques well known to those skilled in this art. The components of the vectors such as the bacterial replicons, selection genes, enhancers, promoters, and the like may be obtained from natural sources or synthesized by known procedures. See Kaufman et al., J. Mol. Biol., 159:601–621 (1982); Kaufman, Proc Natl. Acad. Sci. 82:689–693 (1985). Eucaryotic expression vectors useful in producing variants of this invention may also contain inducible promoters or comprise inducible expression systems as are known in the art. See e.g., "High Level Inducible Expression of Heterologous Genes", International Application No. PCT/US87/01871, the contents of which are incorporated herein by reference.

Established cell lines, including transformed cell lines, are suitable as hosts. Normal diploid cells, cell strains derived from in vitro culture of primary tissue, as well as primary explants (including relatively undifferentiated cells such as haematopoetic stem cells) are also suitable. Candidate cells need not be genotypically deficient in the selection gene so long as the selection gene is dominantly acting.

The host cells preferably will be established mammalian cell lines. For stable integration of the vector DNA into chromosomal DNA, and for subsequent amplification of the integrated vector DNA, both by conventional methods, CHO (Chinese Hamster Ovary) cells are presently preferred. Alternatively, the vector DNA may include all or part of the bovine papilloma virus genome (Lusky et al., Cell, 36: 391–401 (1984) and be carried in cell lines such as C127 mouse cells as a stable episomal element. Other usable mammalian cell lines include Hela, COS-1 monkey cells, melanoma cell lines such as Bowes cells, mouse L-929 cells, 3T3 lines derived from Swiss, Balb-c or NIH mice, BHK or HaK hamster cell lines and the like.

C. Plasmid Constructions

Plasmid pMT2 may be obtained by EcoRI digestion of pMT2-VWF, which has been deposited with the American Type Culture Collection under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods.

The following Examples are set forth to better illustrate the invention, and are not intended to, and should not be construed to limit the scope of this invention as defined in the claims which follow thereafter. The Examples show, inter alia: (i) the high level expression of wild type and mutant (Ala-48, Ala-51 and Ala-48,51) eIF-2α in eucaryotic cells such as COS-1 cells; (ii) that translation of eIF-2α is not affected by the presence of adenovirus VA RNA; (iii) that expression of wild type eIF-2α does not dramatically alter translation of other mRNAs; and, (iv) that expression of the Ala mutants of eIF-2α potentiates translation of mRNAs derived from transfected plasmids but has no effect on total host protein synthesis.

EXAMPLE 1

Construction of the eIF-2a Expression Plasmid

The plasmids used in these experiments are described in Table I. The expression vectors for eIF-2a are pMT2 and pMT2VA−. Plasmid pMT2 may be obtained by Eco RI digestion of pMT2-VWF (ATCC accession number 67122). pMT2 and pMT2VA− contain the SV40 origin of replication and transcriptional enhancer, the adenovirus major late promoter, the majority of the tripartite leader present on adenovirus late mRNAs, a DHFR sequence present in the 3' end of the transcript, and the SV40 early polyadenylation signal. They contain the beta lactamase gene and the Col El origin of replication for selection and replication in E. coli. Both plasmids have unique EcoRI cloning sites for insertion of cDNA clones. Both plasmids are identical except that pMT2VA− does not contain the adenovirus VA genes. pMT2VA− is an identical plasmid that lacks the adenovirus VA genes by deletion of sequences from the Bam HI site at position 2058 to the SacI site at position 2659, with respect to the HindIII site within the SV40 origin/enhancer element at position 1. The eIF-2a cDNA was excised from pSP65-2alpha (Ernst, H., Duncan, R. F., and J. W. B. Hershey 1987, J. Biol. Chem. 262: 1206-1212) by digestion with HincII and addition of EcoRI adapters having the sequence:
3' GAGATCTCAGCTGCCTTAA-P 5'
5'-P-CTCTAGAGTCGACGG-OH 3'
After ligation, the DNA was digested with Eco RI and the 1.6 kB fragment was isolated after agarose gel electrophoresis and ligated to pMT2VA− and pMT2 which had previously been digested with Eco RI and treated with calf intestine phosphatase. The ligated DNA was transformed into E. coli DH5 and plated onto bacterial plates containing 50 ug/ml of ampicillin. DNA was prepared from transformants and screened for the presence of the eIF-2a sequence in the correct orientation by restriction endonuclease digestion and gel electrophoresis. Two clones were obtained, pMT2VA−eIF-2 (herein described as peIF−) and pMT2eIF-2 (herein described as peIF+). pMT2VA−eIF-2 had deleted the 3' Eco RI site upon cloning and has been deposited with the ATCC (ATCC accession number 67511).

TABLE II

| | Plasmids used in this study | | |
|---|---|---|---|
| Vector Name | eIF-2a | Selectable Marker | VA Genes |
| (A) pMT2 | — | DHFR | + |
| (B) pMT2VA− | — | DHFR | — |
| (C) pMT2eIF2a (peIF+) | wild-type | only weak DHFR, polycistronic | + |
| (D) pMT2VA−eIF2a (peIF−) | wild-type | only weak DHFR, polycistronic | — |
| (E) pMT2VA−eIF48 (p48) | 48, ala | only weak DHFR, polycistronic | — |
| (F) pMT2VA−eIF51 (p51) | 51, ala | only weak DHFR, polycistronic | — |
| (G) pMT2VA−eIF48/51 (p48/51) | 48, ala 51, ala | only weak DHFR, polycistronic | — |
| (H) pD61 | — | DHFR | — |
| (I) p91023(B) | — | DHFR | + |
| (J) pMT2SVADA | — | ADA | + |

EXAMPLE 12

Construction of eIF-2a mutants at positions 48, 51, and 48/51

Oligonucleotide directed mutagenesis was performed to change the serine at amino acid position 48 and at 51 to an alanine. Three mutagenic oligonucleotides of the sequences:
wildtype: 5'-GGATACGCCTTCTGGATAATTCT-CAAAGCCGAATCATGCCTTC
(A) 48 ala: 5'-CGCCTTCTGGATAATTCAG CAAGCCGAATCATGCCTTC
(B) 51 ala: 5,-GGATACGCCTTCTGGCCAATTCT-CAAAGAAG
(C) 48/51 ala: 5'-GGATACGCCTTCTGGCCAATT-CAGCAAGAAG
were synthesized and used for mutagenesis using the heteroduplex procedure of Morinaga et al (Biotechnology 1984, 84: 636.). 10 ug of pMT2VA−eIF-2a was digested with NdeI which cuts the plasmid once outside the eIF-2a sequences and then treated with calf intestine phosphatase. 10 ug of pMT2VA− was digested with Eco RI and similarly treated with calf intestine phosphatase. Each preparation of DNA was electrophoresed on low temperature melting agarose gels and the linear forms isolated by adsorption to and extraction from silica dioxide. One ug of each preparation were mixed and denatured in a volume of 20 ul of 0.2N NaOH at room temperature for 10 min. The mixture was subsequently neutralized with 180 ul of 0.02N HCl/0.1M TrisOHCl pH 8.0. 20 picomoles of the phosphorylated mutagenic oligonucleotide was added to 40 ul of the heteroduplex mixture and placed at 68° C. for 90 min. After the incubation the mixture was slowly cooled to room temperature. Each mutagenic reaction was addjusted to 2 mM $MgCl^2$, 1 mM beta-mercaptoethanol, 400 uM ATP, 100 uM of each deoxyribonucleotide triphosphates, 3–4 units of Klenow fragment of E. coli DNA polymerase I, and 400 units of T4 DNA ligase. The reactions were incubated for 10 min at room temperature and then transferred to 16° C. for incubation overnight. Reactions were terminated by phenol-chloroform (1:1) extraction and then precipitated by the addition of ethanol. The DNA was then used to transform E. coli DH5 and the ampicillin resistant transformants were screened for hybridization to the following screening oligonucleotides which were radiolabeled with T4 polynucleotide kinase and gamma-$^{32}PO_4$ ATP:
(A) 48- 5' TCTTCTTGCTGAATTA -3'
(B) 51- 5' 5-CTGAATTGGCCAGATC-3'
(C) 48/51: 5- CTGAATTGGCCAGAAG-3'
Filter hybridizations were performed at 37° in 5× SSC (1× = 150 mM |NaCl, 15 mM Na citrate) with 5× Denhardt's reagent, 0.1% sodium dodecyl sulfate, and 100 ug/ml salmon sperm DNA for 12 hrs. Filters were washed in 5× SSC with 0.1% SDS at 37° C. and then prepared for autoradiography. Positively hybridizing clones were identified, DNA was isolated, and retransformed into E. coli for further analysis. Mutations were confirmed by oligonucleotide Southern hybridization, digestion with frequent cutting restriction endonucleases, and sequencing by the collapsed coil method of dideoxy nucleotide sequencing using an oligonucleotide (5'- GACAACCACACACTCA -3') as a primer. The eIF-2a expression plasmids harboring the correct changes are pMT2-VA−eIF2a48, pMT2-VA−eIF2a51, and pMT2-VA−eIF2a48/51, respectively as in Table II and from herein will be designated p48, p51, and p48/51.

EXAMPLE III

Expression of Wildtype and Variants of eIF-2a in COS-1 cells

Plasmids peIF−, peIF+, p48, p51, and p48/51 were transfected into COS-1 cells using the DEAE dextran procedure (Sompayrac, L. M, abd K. J. Dana 1981, Proc. Natl. Acad. Sci. 78: 7575). DNA (2 ug/ml) was prepared in Dulbecco's Minimal Essential medium (DME) containing 250 ug/ml of DEAE dextran, 0.1M Tris-HCl pH 7.3. COS-1 cells that were plated 20 hr previously were rinsed with serum free media and fed the media containing DNA. Cells were incubated for 6-12 hr at 37° C. and then the medium was removed and 10% dimethyl sulfoxide (DMSO) added for 4 min. The DMSO was removed and medium containing 1 mM chloroquin was added. After 2 hr at 37° the chloroquin was removed and DME medium containing 10% fetal calf serum was applied. 72 hr. later cells were labeled in methionine-free DME medium containing $^{35}$S-methionine (100 uCi/ml of $^{35}$S-methionine, 7800 Ci/mmol, New England Nuclear Corp.) for 30 min at 37° C. After this incubation, cell extracts were prepared by lysis in RIPA buffer (Kaufman and Sharp, 1982, J. Mol. Biol. 159: 601) containing 1 mM phenylmethyl sulfonyl fluoride and the extracts were analyzed by electrophoresis on 12.5% polyacrylamide gels. Analysis of the radiolabeled proteins from the eIF-2a expression plasmids containing the wild-type and the mutations show significant amounts of the eIF-2a protein which migrates at 36 kDa. Immunoprecipitation of these samples with a sheep anti-human eIF-2a antisera (provided by Brian Safer) give similar results.

Analysis of the mRNA present in the transfected cells by Northern blot hybridization analysis demonstrated that each eIF-2a expression plasmid produced similar amounts of eIF-2a specific mRNA. The level of the eIF-2a mRNA parallels the level of the eIF-2a protein synthesis in transfected cells in either the presence and absence of VA RNA. These results are in contrast to the expression of other cDNA introduced into COS-1 cell expression vectors where the translation of the plasmid derived mRNA is increased by the presence of the VA RNA. Interestingly, the translation of eIF-2a was not increased by the presence of the VA genes in peIF+. This represents the first example of an mRNA expressed from an expression vector in COS-1 cells which is efficiently translated in the absence of the VA genes. This suggests that the eIF-2a mRNA has evolved signals which result in its efficient translation in the presence of eIF-2a phosphorylation.

EXAMPLE 4

Phosphorylation State of eIF-2a Protein Expressed in COS-1 Cells

The phosphorylation state of the eIF-2a protein expressed in COS-1 cells was monitored by labelling COS-1 transfected cells at 66 hr post transfection with 0.5 mCi/ml of $^{32}$PO$_4$ (New England Nuclear,) (2 ml of 200 uCi/ml for 4 hr or 1 ml or 1 mCi/ml for 20 min) in phosphate free medium. Extracts were prepared and immunoprecipitated with the sheep anti-human eIF-2a antisera using protein A sepharose as the immunoadsorbant. Samples were electrophoresed on 12.5% polyacrylamide SDS gels. Gels were fixed and prepared for autoradiography. The results demonstrate that all eIF-2a forms incorporate PO$_4$ after 4 hr. The nature of the modification responsible for incorporation of this phosphate is not known. In contrast, when analyzed after 20 min of phosphate labeling, the peIF− and the p48 exhibit PO$^4$ incorporation, whereas the other peIF(+), p51, and p48/51 incorporate negligible phosphate. This is consistent with the notion that the 51 serine is the phosphorylation site for DAI kinase and that the VA genes present in peIF+ can inhibit the phosphorylation mediated by DAI kinase.

The capability of the various forms of eIF-2a to serve as substrates for the heme controlled repressor kinase was examined by preparing extracts of COS-1 transfected cells 72 hr post-transfection. Cells were lysed in 20 mM Tris HCl pH 7.4, 100 mM KCl, 2 mM MgCl$_2$, and 0.5% PN40 and aliquots taken for in vitro kinase reactions in the presence of added ATP and HCR kinase (provided by John Hershey). After 15 min at 30° C., aliquots were electrophoresed on 12.5% polyacrylamide gels and the gels were prepared for autoradiography. Results demonstrate that the eIF-2a expressed from peIF+, peIF−, and p48 all serve as substrates for the HCR kinase. In contrast, the eIF-2a expressed from p51 or p48/51 do not incorporate phosphate. This result is consistent with the notion that the 51 ser to ala mutation blocks the phosphorylation mediated by HCR kinase.

EXAMPLE 5

Coexpression of Wt and Mutants of eIF-2a with DHFR in the Presence and Absence of the VA Genes In order to determine whether increased expression of either of the wildtype or mutant forms or eIF-2a can potentiate translation of an mRNA in COS-1 cells the following experiment was performed. I have previously demonstrated that expression of dihydrofolate reductase from plasmid pD61 transfected into COS-1 cells is low as a result of inefficient translation of the mRNA (Kaufman, 1985, Proc. Natl. Acad. Sci. 82: 689). This inefficient translation can be over come by coexpression of the adenovirus VA genes. In order to determine if any of the eIF-2a proteins are capable of potentiating translation of the DHFR mRNA from pD61, the different eIF-2a expression plasmids were contransfected with pD61 into COS-1 cells and translation of DHFR was studied. For this experiment, 8 ug of pD61 and of each of the different eIF-2a expression plasmids were mixed and transfected into COS-1 cells as described in Example 3. At 72 hr post-transfection, the cells were labeled with $^{35}$S-methionine (100 uCi/ml of methionine-free DME medium) for 20 min and cell extracts prepared by lysis in RIPA buffer as described (Kaufman and Murtha, Mol. Cell. Biol. 7: 1568, 1987). Total cell extracts were electrophoresed on 15% polyacrylamide SDS gels and the gels prepared for autoradiography. Analysis of the results demonstrated that DHFR synthesis, which is detected as a band migrating at 20 kDa, is 7–10 fold greater in cells where pD61 is transfected with p48, p51, or p48/51 in contrast to when pD61 is transfected with the wildtype eIF-2a expression vector p−. With cotransfection of either of the eIF-2a mutants, the level of DHFR synthesis is even greater than that observed with p91023(B), a DHFR expression plasmid identical to pD61 except that it contains the adenovirus VA genes. Thus, all the mutant eIF-2a forms tested can enhance DHFR synthesis to a greater extent than that obtained by expression of VA RNA to inhibit DAI kinase. It is surprising that pMT2VA−eIF-2a48 exhibits a similar effect as pMT2VA−eIF2a51 since it can serve as a substrate for phosphorylation by DAI and HCR kinase whereas the eIF-2a from pMT2VA−eIF2a51 cannot. It is not understood why the 48 mutant can enhance the translation of DHFR mRNA.

The level of mRNA encoding eIF-2a and DFHR in the above experiment was monitored by preparing a duplicate plate of transfected COS-1 cells and isolating RNA at 72 hr post-transfection. Analysis by Northern blot hybridization to either DHFR or eIF-2a specific probes prepared by nick-translation demonstrated that the level of the DHFR mRNA was not responsible for the increased translation observed by cotransfection of the mutant forms of eIF-2a.

EXAMPLE 6

Sequences in the 5′ End of eIF-2a mRNA are Responsible for the Ability of the eIF-2a mRNA to be Translated in the Absence of VA RNA In order to determine whether specific sequences within the eFI-2a mRNA may mediate the efficient translation in the presence of eIF-2a phosphorylation, the effect of their deletion was studied. The 5′ untranslated region of the eIF-2a mRNA was deleted by the following procedure. First, pMT2 was digested with EcoRI and treated with calf intestine phosphatase. The linear form was isolated by electrophoresis on a low melting temperature agarose gel. A second fragment encoding the majority of eIF-2a but lacking the AUG and first base of the second codon was prepared by digestion of peIF− with HpaII and Eco RI (Note the plasmid used in this construction had restored the Eco RI site at the 3′ end of eIF-2a within the adapter adjoining the insert to the vector, see example 1). The 900 bp fragment was isolated by electrophoresis on a low melting temperature gel. Finally a linker (EcoRI-HpaII) was synthesized that contains the AUG codon and restores the second amino acid for eIF-2a having the sequence:

5′ P-AATTCACCATGC-3′
3′-GTGGTACGGC-P 5′

The linker was phosphorylated at both ends using T4 polynucleotide kinase and 10 mM ATP. A ligation was performed using equimolar amounts of each isolated fragment and the linker. DNA was transformed into E. coli DH5 and transformants screened by filter hybridization to a probe prepared by nick-translation of the eIF-2a fragment described above. DNA was prepared from positively hybridizing clones and tested for orientation of the Eco RI fragment insert into pMT2 by digestion with Hpa II and BamHI. A clone harboring the correct orientation of the eIF-2a insert was identified as peIF2-5′. DNA was prepared for sequencing by dideoxynucleotide chain termination method of Sanger et al in order to confirm the proper sequence of the clone obtained.

To analyze the effect of deletion of the 5′ end of eIF-2a, COS-1 cells were transfected with peIF2-5′ and peIF− 72 hr post transfection, cells were labeled with $^{35}$S-methionine in methionine-free medium and extracts prepared for analysis on 12.5% polyacrylamide SDS gels. In addition, RNA was prepared for RNA blot hybridization analysis using an eIF-2a probe prepared by nick-translation of the eIF-2a cDNA fragment. The results demonstrate that eIF2a translation from the 5′ deleted vector (peIF-5′) is decreased several fold compared to the original peIF− plasmid. Thus, the sequences in the 5′ end of the eIF-2a mRNA are required to potentiate translation of the eIF-2a mRNA in transfected COS-1 cells. These sequences appear important for translation of mRNA in the presence of eIF-2a phosphorylation.

EXAMPLE 7

The 5′ End of the eIF-2a mRNA can Potentiate Translation of a Heterologous mRNA.

In order to determine if the 5′ end of the eIF-2a mRNA can potentiate translation of another mRNA, a several overlapping ologonucleotides were synthesized to construct the following sequence:

5′
P-AATTCAAGTCTGGTCTCTGTGATTGAAGAAGTCGGCTCTGGGCTCCAGTGCGGGAATCACA

CACATACCTCAGAATGCCGA -3′

This sequence represents the first 72 bases of the eFI-2a mRNA upstream from the AUG, including the first two amino acids with 5′ Eco RI protruding ends. This Eco RI linker was inserted into an adenosine deaminase (ADA) expression vector p9a which has an Eco RI site at the start site for translation initiation. p9A has previously been described (Kaufman et al. 1987 EMBO J. 6: 187–193). Expression of ADA from p9a is low as a result from inefficient translation of the mRNA in COS-1 cells. The level of expression can be increased by cotransfection of the adenovirus VA genes (Kaufman and Murtha, Mol. Cell. Biol. 1987). The Eco RI linker described above was phosphorylated with T4 DNA polynucleotide kinase and ligated to EcoRI digested and calf intestine phosphatase treated p9A DNA. The ligated DNA was transformed into E. coli DH5 and the bacteria plated onto plates containing 15 ug/ml of tetracycline. Colonies were screened by hybridization to the original oligonucleotide which was labeled by a T4 DNA polynucleotide kinase reaction using gamma $^{32}$P-ATP. Positively hybridizing clones were identified and DNA prepared. The orientation of the insert was determined by digestion with Eco RI and BamHI and electrophoresis of the plasmid DNA on agarose gels for Southern blot hybridization to the labeled oligonucleotide. The clones harboring the correct orientation exhibit hybridization to a 2.4 kB band. Two clones were identified, one with the correct orientation p9A-5′eIF2 and one with the incorrect orientation p9A-5′eIF2b of the inserted oligonucleotide with respect to the orientation in peIF−, and DNA was prepared for confirmation by DNA sequencing.

In order to analyze the effect of insertion of the 5' untranslated sequences of the eIF-2a mRNA into a heterologous mRNA, the ADA expression plasmids p9A, p9ADA5-29 (a plasmid identical to p9A but which contains the VA genes), p9A-5'eIF-2b and p9A-eIF2 were transfected into COS-1 cells as described in Example 3. ADA synthesis was monitored at 72 hr post-transfection by labelling with $^{35}$S-methionine for 30 min. Cell extracts were prepared by lysis in RIPA buffer and protein synthesis was examined by electrophoresis on a 10% polyacrylamide SDS gel and autoradiography. Results demonstrated that insertion of the 5' untranslated region of eIF-2a into the ADA expression plasmid can enhances translation of the ADA mRNA in the absence of the VA genes. The plasmid harboring the incorrect orientation of the linker insert did not result in increased translation.

EXAMPLE 8

Introduction of eIF-2a Wt and Mutants into 293 Cells

Plasmid DNA was introduced into human adenovirus transformed 293 cells by the calcium phosphate coprecipitation method of DNA transfection. 10 ug of each plasmid peIF—, p48, p51, and p48/51 were mixed with 1 ug of pSV2Neo (Southern and Berg,) and 1 ug of pD61 and precipitated with CaPO$_4$ as described (Kaufman and Sharp, J. Mol. Biol. 159: 601, 1982). The CaPO$_4$ precipitate was applied to 293 cells for 30 min and at room temperature and then 10 volumes of DME medium was applied. The cells were incubated 4 hrs at 37° and then the mixture removed and the cells treated with 10% glycerol in DME medium for 4 min at room temperature. The glycerol was rinsed from the cells and DME medium containing 10% fetal calf serum was applied. 48 hrs later the cells were subcultured ⅛ into medium containing 1 mg/ml of G418 for selective pressure for the pSV2Neo. 17 days later colonies appeared on all transfected plates whereas cells that did not receive DNA did not form G418 resistant colonies. Individual clones were either picked or pooled. These transformants were then grown in 0.3 uM methotrexate to select for cells that had amplified the transfected DHFR gene from p91023(B). Under these conditions, the original 293 cells do not grow, whereas cells transfected with p91023(B) form colonies. Cells are then propagated in sequentially increasing concentrations of methotrexate in order to obtain cells that express increasing levels of eIF-2a which result from coamplification of the eIF-2a expression plasmid.

Expression of eIF-2a in 293 cells is monitored by analysis of the mRNA by Northern bot hybridization and by Western protein gel blotting procedures. The probe for the Northern hybridization is the nick-translated eIF-2a cDNA. The probe for the Western is the sheep anti-human rabbit eIF-2a and then developed with 125-iodinated protein A. For Northern analysis, a new mRNA species is detected in some the G418 resistant colonies that is not present in the original 293 cells. This species becomes amplified in cells selected further by growth in 0.3 uM methotrexate. Analysis by Western blotting indicates that some of the transfected cells express higher levels of a species migrating at 36 kDa. This becomes further amplified in cells selected for growth in 0.3 uM methotrexate. It has been observed that cells which express the modified forms of eIF-2a can grow at greater rate than the original 293 cells or than 293 cells that express higher levels of the wildtype eIF-2a. This effect may result from the translational suppression imposed in cells in response to eIF-2a phosphorylation.

EXAMPLE 9

293 Cells that Express the Mutant eIF-2a can Support the Growth of VA Deficient Adenoviruses In order to monitor any effect the expression of the wildtype and phosphorylation resistant mutants of eIF-2a in 293 cells, we have monitored the ability of these cells to support the replication of adenoviruses that are mutant in that VA genes (dl331, Thimmappaya et al. 1982, Cell 31: 543). Adenovirus infection was performed and monitored by pulse labeling cells at 36 hr post infection with $^{35}$S-methionine and analysis of the cell extracts for viral late protein synthesis by SDS polyacrylamide gel electrophoresis. The original 293 cells or 293 cells that express elevated levels of the wildtype eIF-2a cannot support the efficient replication of adenovirus dl331, compared to the wildltype adenovirus. In contrast, 293 cells that express either the 48 or the 51 mutants of eFI-2a can support the growth of adenovirus dl331, in a similar manner to wildtype adenovirus.

The effect of the eIF-2a mutants expressed in 293 can also be observed by transient DNA transfection. For this experiment pD61 and p91023(B), which are identical DHFR expression plasmids except for the presence of the VA genes in p91023(B), are transfected into wildtype 293 cells and into 293 cells which express the wildtype eIF-2a and the 48 and the 51 eIF-2a mutants by DEAE-mediated DNA dextran transfection. 48 hr later the cells, are labeled with $^{35}$S-methionine and cell extracts prepared for analysis by immunoprecipitation with a rabbit anti-mouse DHFR antisera and SDS-polyacrylamide gel electrophoresis. The results demonstrate that 293 cells that have either mutant eIF-2a can express higher levels of DHFR from pD61 compared to the wildtype 293 cells or 293 cells that express the wildtype eIF-2a. Transfection of p91023(B) results in high similar levels of DHFR expression in all cells. Northern blot analysis of the RNA with a DHFR probe indicated that all cells have the same level of the DHFR mRNA. These results are consistent with the notion that the mutant eIF-2a protein can increase translation in the pD61 plasmid whereas p91023(B) can utilize the VA genes to potentiate translation.

EXAMPLE 10

Introduction of eIF-2a Wt and Mutants into CHO Cells

In order to introduce the wildtype and mutant eIF-2a genes into CHO cells, an expression vector which has adenosine deainase as the selectable marker was used. Plasmid pMT2ADA is obtained from pMT2ADAVWF (ATCC #67172) by partial digestion with Eco RI and religation to remove the VWF sequences. This plasmid is then digested with EcoRI and the Eco RI fragments encoding the wildtype and mutant forms of eIF-2a are isolated by EcoRI digestion and inserted into the EcoRI site of pMT2ADA which had previously been digested with EcoRI and treated with calf intestine phosphatase. The DNA is used to transform *E. coli* to ampicillin resistance and the colonies grown for analysis of the DNA by restriction endonuclease digestion. The plasmids harboring the correct orientation of the eIF-2a in the ADA expression plasmid are called pMT2ADA-eIF2a, pMT2ADA-eIF248, and pMT2ADA-eIF251.

*E. coli* DH5 harboring the above plasmids are grown to prepare protoplasts for fusion to CHO cell line D2 which express high levels of GM-CSF as a result of amplification of the GM-CSF gene with DHFR. Protoplast fusions are performed as is known in the art and 48 hr later the cells are subcultured into ADA selection media containing 4 uM xyol A and 0.03 uM deoxycoformycin. This selection protocol is described previously (Kaufman et al., 1986 Proc. Natl. Acad. Sci. 83: 3136). Then the DNA is amplified by selection for growth in medium containing 11 mM adenosine and increasing levels of 2'deoxycoformycin. The final cells obtained which express high levels of the mutant eIF-2α genes may be used for the expression in higher levels of GM-CSF. Expression of the wildtype eIF-2α should have little effect on GM-CSF expression.

What is claimed is:

1. A eucaryotic host cell containing a DNA molecule encoding the polypeptide sequence of an eIF-2α, said DNA molecule being operatively linked to an expression control sequence permitting expression of the eIF-2α protein, said eIF-2α protein being characterized by the peptide sequence of Table 1 with a modification selected from the group consisting of:
    (a) deletion of ser-48 or replacement thereof with a different amino acid,
    (b) deletion of ser-51 or replacement thereof with a different amino acid, and
    (c) both (a) and (b) wherein said modification results in a modified eIF-2 protein which is capable of supporting the growth of a VA deficient strain of adenovirus in 293 cells substantially as well as the corresponding wild type adenovirus.

2. A eucaryotic host cell of claim 1, wherein said DNA molecule is present in multiple copies.

3. A eucaryotic host cell of claim 2 which further contains a second heterologous DNA sequence encoding a heterologous protein operatively linked to an expression control sequence permitting expression of the heterologous protein.

4. A eucaryotic host cell of claim 3 wherein the host cell is a mammalian host cell.

5. A host cell of claim 4 wherein the host cell is a COS-1, CV-1, CHO, NIH 3T3, or human cell line.

6. A method for producing a heterologous protein which comprises culturing a eucaryotic cell of claim 3.

7. A method for producing a heterologous protein which comprises culturing a mammalian cell of claim 4.

8. An expression vector containing (i) the eIF-2α5' untranslated DNA sequence linked to (ii) the 5' terminus of a DNA sequence containing therein a nucleotide sequence encoding a heterologous protein and which is operatively linked to an expression control sequence permitting expression of the heterologous protein.

9. A eucaryotic host cell containing the vector of claim 8.

10. A method for producing a heterologous protein which comprises culturing a cell of claim 9 under suitable conditions permitting production of the protein.

* * * * *